United States Patent [19]

Kobayashi et al.

[11] Patent Number: 4,585,731

[45] Date of Patent: Apr. 29, 1986

[54] SILVER HALIDE COLOR PHOTOGRAPHIC LIGHT-SENSITIVE MATERIAL

[75] Inventors: Hidetoshi Kobayashi; Keiji Mihayashi, both of Kanagawa, Japan

[73] Assignee: Fuji Photo Film Co., Ltd., Kanagawa, Japan

[21] Appl. No.: 639,294

[22] Filed: Aug. 10, 1984

[30] Foreign Application Priority Data

Aug. 10, 1983 [JP] Japan ................................. 58-146097

[51] Int. Cl.[4] ................................................ G03C 7/26
[52] U.S. Cl. ..................................... 430/543; 430/553; 430/555; 430/557; 430/558; 430/598; 430/955
[58] Field of Search ............... 430/543, 553, 555, 557, 430/558, 955, 598

[56] References Cited

U.S. PATENT DOCUMENTS

| 4,358,525 | 11/1982 | Mooberry et al. | 430/955 |
| 4,390,618 | 6/1983 | Kobayashi et al. | 430/543 |
| 4,420,556 | 12/1983 | Booms et al. | 430/549 |

Primary Examiner—J. Travis Brown
Attorney, Agent, or Firm—Sughrue, Mion, Zinn, Macpeak and Seas

[57] ABSTRACT

A silver halide color photographic light-sensitive material is disclosed, comprising a support having thereon at least one silver halide emulsion layer, wherein at least one silver halide emulsion layer contains a coupler which is subjected to a coupling reaction with an oxidation product of a color developing agent to produce a diffusible coupling product which exerts a fogging effect in a developing solution; the silver halide color photographic light-sensitive material provides increased contrast and sensitivity, development is accelerated, and stability during storage is improved.

18 Claims, No Drawings

SILVER HALIDE COLOR PHOTOGRAPHIC LIGHT-SENSITIVE MATERIAL

FIELD OF THE INVENTION

This invention relates to a silver halide color photographic light-sensitive material containing a compound capable of imagewise releasing a fogging agent by which the contrast and sensitivity are increased, the development is accelerated, and the stability during storage is improved, and to a method of forming a color image using such a compound.

BACKGROUND OF THE INVENTION

It is well known that color images can be obtained by exposing a silver halide color photographic light-sensitive material to light, followed by a reaction between an oxidized aromatic primary amine developing agent and a dye forming coupler. In such a process, the subtractive color process is usually adopted for color reproduction, and cyan, magenta and yellow color images, which are complementary to red, green, and blue colors, respectively, are formed. The reaction between a coupler and an oxidation product of a color developing agent proceeds at an active point of the coupler. A coupler having a hydrogen atom at its active point (i.e., a 4-equivalent coupler) stoichiometrically requires as an oxidizing agent 4 mols of a silver halide having a development center for forming 1 mol of a dye through the coupling reaction. On the other hand, a coupler having at its active point a group capable of being released in the form of an anion requires only 2 mols of a silver halide having a development center for forming 1 mol of a dye (i.e., a 2-equivalent coupler). Accordingly, by using a 2-equivalent coupler, the amount of silver halide to be used in a light-sensitive layer can be reduced and the layer per se can be made thinner, so that the time required for the processing of such a light-sensitive material can be shortened and color images obtained therefrom have an improved sharpness, when compared with a light-sensitive material in which a 4-equivalent coupler is used. In addition, the coupling activity of a 2-equivalent coupler with a color developing agent can be widely varied depending on the properties of the releasable group contained therein.

A 2-equivalent coupler capable of releasing a group having a development-inhibiting effect is called a development inhibitor releasing coupler (or DIR coupler). Such a coupler is capable of inhibiting development in proportion to the quantity of developed silver, and therefore is effective to improve graininess, gradation control, color reproducibility of images, etc. Couplers of this type can also be used in diffusion transfer processes, making use of their effects upon adjacent layers.

A 2-equivalent coupler can also be provided with a releasable group containing a diffusible dye portion. This type of couplers, which are referred to as diffusible dye-releasing couplers, can be utilized in a diffusion transfer process in which a dye image is formed from diffused dyes in an image receiving layer.

Certain colored 2-equivalent couplers have a masking effect for color correction of dye images and are usually called colored couplers.

As mentioned hereinbefore, 2-equivalent couplers can be imparted with various functions by appropriately selecting the releasable groups contained therein.

In recent development of silver halide photographic light-sensitive materials, especially, those for photographing, two outstanding trends are observed. One is the increase in sensitivity as typically shown by ASA 400 films, and another is the improvement in image quality to cope with the miniaturization of film sizes. In connection with the former, investigations have been made on a variety of techniques including large-sized silver halide grains, couplers with higher activities, acceleration of development, etc. However, increases in sensitivity based on large-sized silver halide grains seem to be reaching its limit, as reported by G. C. Farnell and J. B. Chanter in *J. Photogr. Sci.*, 9, 75 (1961). Accordingly, this technique is not expected to make much progress in the future. In addition, the use of large-sized silver halide grains is accompanied by various disadvantages such as deterioration in graininess. Couplers having higher activities have also been studied extensively, but have not made such contribution to sensitivities of silver halide photographic light-sensitive materials, and are also disadvantageous with respect to graininess. With respect to acceleration of development, it has hitherto been attempted to incorporate various development accelerators, such as hydrazine compounds, into a silver halide emulsion layer or a developing solution mainly with regard to black-and-white photographic light-sensitive materials. However, such a technique is not practical as being often accompanied by disadvantages, such as increase in fog, deterioration in graininess, and the like.

Under such circumstances, couplers which imagewise release development accelerators or fogging agents have been proposed. For example, couplers releasing thiocyanic acid ions which accelerate the solution physical development are disclosed in U.S. Pat. Nos. 3,214,377, 3,253,924 and 4,032,345. Further, couplers releasing acyl hydrazines are described in U.S. Pat. No. 4,390,618 and couplers releasing hydroquinone or aminophenol developing agents are described in Japanese Patent Appliction (OPI) No. 138636/82 (the term "OPI" as used herein refers to a "published unexamined Japanese patent application").

U.S. Pat. No. 4,390,618 and U.S. patent application Ser. Nos. 532,631 (filed on Sept. 15, 1983) and 583,901 (filed on Feb. 27, 1984) disclose couplers releasing fogging agents and furnish details of the effects brought about by the imagewise release of the fogging agents on contrast or development acceleration. However, most of these couplers have low stability, and they undesirably cause deteriorations in photographic properties, such as a general increase in fog, desensitization during storage, and their effects reduce with the passage of time when they are incorporated into silver halide photographic light-sensitive materials. Moreover, these couplers have been found to deteriorate graininess as compared with photographic light-sensitive materials into which these couplers are not incorporated to increase contrast and sensitivity.

On the other hand, in order to improve graininess, attempts have been made to use a larger number of silver halide grains and to shade off the dye clouds formed by color development, as described in *The Theory of the Photographic Process*, 4th Ed., 1977, pp. 620–621, edited by T. H. James. However, to use a larger number of silver halide grains while retaining photographic sensitivity means an increased amount of silver must be applied, which results in deterioration of resolving power. Hence, such a technique is disadvantageous from the standpoint not only of cost, but also photographic properties.

Further, an attempt to improve graininess by diffusion of dyes according to the description in the above-cited James text has already been disclosed in British Pat. No. 2,080,640A. However, it has been proved that such couplers releasing diffusible dyes have reduced coupling activities, resulting in reduction of coloring density or sensitivity and increase of fog with the passage of time.

Furthermore, the above-described couplers are synthesized by introducing fogging agents into the releasable groups, and therefore the releasable groups or the coupler centers are limited so that sufficient coupling activities to attain the desired effects cannot be obtained.

SUMMARY OF THE INVENTION

Accordingly, a first object of this invention is to provide a silver halide photographic light-sensitive material having high sensitivity and improved graininess.

A second object of this invention is to provide a silver halide photographic light-sensitive material having high contrast.

A third object of this invention is to provide a silver halide photographic light-sensitive material which can be rapidly processed.

A fourth object of this invention is to provide a silver halide photographic light-sensitive material having excellent stability during storage.

A fifth object of this invention is to provide a silver halide photographic light-sensitive material which can be prepared with a wide selection of the releasable groups or coupler centers so that the desired effects such as high contrast can easily be obtained.

As a result of extensive investigations, it has now been found that the above-described objects of the present invention can be achieved by incorporating a nondiffusible coupler, which when subjected to a coupling reaction with an oxidation product of a color developing agent produces a diffusible coupling product and exerts a fogging effect in a developing solution, into at least one photographic emulsion layer of silver halide photographic light-sensitive materials.

Accordingly, in accordance with the present invention there is provided a silver halide color photographic light-sensitive material comprising a support having thereon at least one silver halide emulsion layer, wherein at least one silver halide emulsion layer contains a coupler represented by formula (I):

COUP—FOG (I)
|
BALL wherein COUP represents a coupler residue capable of being subjected to a coupling reaction with an oxidation product of an aromatic primary amine developing ageng; BALL represents a ballast group bonded to the coupling position of COUP and releasable from COUP upon reaction between COUP and an oxidized product of an aromatic primary amine developing agent, the ballast group having such sizes and forms so as to impart nondiffusibility to the coupler; and FOG represents a group which manifests a fogging effect in a developing solution after BALL is released upon the reaction between COUP and an oxidation product of an aromatic primary amine developing agent.

DETAILED DESCRIPTION OF THE INVENTION

The present invention relates to a coupler capable of releasing a diffusible dye which exerts a fogging effect. A detailed description is hereinafter provided on the couplers of the present invention.

In formula (I), the coupler residue represented by COUP can include residues derived from cyan, magenta, yellow, or non-color-forming couplers which are known or have already been employed in the art.

The cyan coupler residues typically include residues of phenol couplers, naphthol couplers, etc. The magenta coupler residues typically include residues of 5-pyrazolone couplers, pyrazolobenzimidazole couplers, pyrazolotriazole couplers, cyanoacetylcoumarone couplers, open chain acylacetonitrile couplers, etc. The yellow coupler residues include residues of acylacetanilide couplers (e.g., benzoylacetanilide couplers, pivaloylacetanilide couplers, etc.), malondianilide couplers, etc. The residues of the non-color-forming couplers, which form, upon reacting with an aromatic primary amine developing agent, a coupling product having no remarkable visible absorption, include residues of open chain or cyclic active methylene compounds (e.g., indazones, cyclopentanones, cyclohexanones, malonic acid diesters, acetophenones, imidazolinones, oxazolinones, thiazolinones, etc.). Hues of the coupling products produced by the reaction between COUP and an oxidation product of an aromatic primary amine developing agent are not limited to the above-described ones.

The group represented by BALL is a so-called ballast group and has such sizes and forms so as to impart nondiffusibility to the coupler. Such a ballast group may be a polymeric group composed of a plurality of releasable groups or a group carrying an alkyl group and/or an aryl group that imparts nondiffusibility. In the latter case, the alkyl group and/or aryl group preferably contains from about 8 to 32 carbon atoms in total. BALL has a linking group to bond to the coupling position of COUP. Typical examples of the linking group include an oxy group (—O—), a thio group (—S—), an azo group (—N=N—), a carbonyloxy group (—OCO—), a sulfonyloxy group (—OSO$_2$—), and an imino group

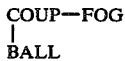

which constitutes part of a heterocyclic ring. Preferred examples of the group represented by BALL are alkoxy, aryloxy, heterocyclic oxy, alkylthio, arylthio, heterocyclic thio, arylazo, acyloxy, alkylsulfonyloxy, arylsulfonyloxy, and hetero rings (e.g., pyrrole, pyrazole, imidazole, triazole, tetrazole, indole, indazole, benzimidazole, benzotriazole, phthalimide, succinimido, 2,4-imidazolidinedione, 2,4-oxazolidinedione, 2,4-thiazolidinedione, triazolidine-3,5-dione, etc.), with the alkyl moiety and/or aryl moiety thereof containing from 8 to 32 carbon atoms in total.

FOG is a partial structure constituting the coupling product having a properly limited mobility which is formed by the reaction with an oxidation product of an aromatic primary amine developing agent, and represents a group exhibiting a fogging effect in a developing solution. Specifically, this group is a group having a partial structure of reducing compounds, e.g., hydrazine, hydrazide, hydrazone, enamine, polyamine, hydroquinone, aminophenol, phenylenediamine, acetylene, aldehyde, etc.; compounds capable of forming silver sulfide, e.g., thiocarbonyl compounds exemplified by thiourea, thioamide, thiocarbamate, dithiocarbamate, rhodanine, thiohydantoin, etc.; or quaternary salt compounds exemplified by tetrazolium salts. FOG contains a divalent linking group for bonding to COUP.

The coupling product is prefered to have properly limited mobility. The expression "properly limited mobility" as used here means a diffusibility to such an extent that it does not cause remarkable reduction in sharpness or adverse influences on layers having different color sensitivities (e.g., color mixing) in case of color negative films, for instance, due to an excess mobility of the coupling product having a fogging effect.

For controlling the diffusibility of the coupling product of the coupler in silver halide emulsion layers or gelatin layers, COUP and/or FOG can be substituted with commonly employed substituents of suitable sizes and forms, e.g., an alkyl group, an alkoxy group, a halogen atom, a carbonamido group, a sulfonamido group, a carbamoyl group, a sulfamoyl group, a carboxyl group, a sulfo group, a sulfonyl group, a hydroxyl group, etc.; or substituents having adsorbability to silver halide, such as groups having structures of azoles (e.g., triazole, tetrazole, benzimidazole, indazole, benzotriazole, etc.), heterocyclic compounds containing a hetero atom in addition to a nitrogen atom (e.g., thiazole, thiadiazole, benzothiazole, benzoxazole, etc.), heterocyclic compounds having a mercapto group (e.g., 2-mercaptobenzothiazole, 2-mercaptobenzoxazole, 2-mercapto-1,3,4-thiadiazole, 1-phenyl-5-mercaptotetrazole, etc.), quaternary salts (e.g., tetrazolium salts, etc.) or thiocarbonyl compounds (e.g., thiourea, thioamide, rhodanine, etc.).

Since the compounds according to the present invention do not contain a fogging agent in their releasable moiety, the releasable group can be selected with wide freedom in their syntheses. Therefore, the coupling activities can be controlled more easily as compared with the compounds described in U.S. Pat. No. 4,390,618, whereby the desired effects such as high contrast, acceleration of development, and the like can easily be attained.

Examples of COUP which can be preferably used in the present invention are shown by the following formulae (II) to (XI):

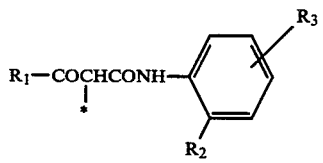
(II)

wherein $R_1$ represents an alkyl group, an aryl group, a heterocyclic group, an alkoxy group, an alkylamino group or an anilino group; $R_2$ represents a hydrogen atom, a halogen atom, an alkyl group, an alkoxy group or an aryloxy group; $R_3$ represents a hydrogen atom, an alkyl group, an alkoxy group, an acyl group, an aryloxy group, a sulfonyl group, a carbonamido group, a hydroxyl group, a carboxyl group, a sulfo group, a sulfonamido group, an alkoxycarbonyl group, a carbamoyl group, a sulfamoyl group, a ureido group or a halogen atom; and * indicates the position at which BALL is bonded;

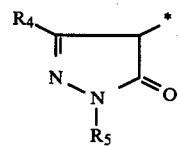
(III)

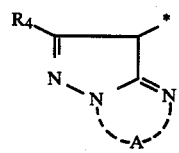
(IV)

wherein $R_4$ represents an alkoxy group, an alkylamino group, a dialkylamino group, an alkyl group, a carbonamido group or a sulfonamido group; $R_5$ represents an alkyl group or an aryl group; A represents a non-metallic atomic group forming a 5-membered azole ring, e.g., an imidazole ring, a triazole ring, a tetrazole ring, etc., and formula (IV) includes tautomers thereof; and * indicates the position at which BALL is bonded;

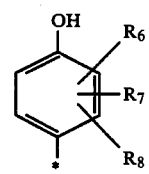
(V)

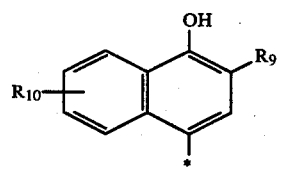
(VI)

wherein $R_6$, $R_7$ and $R_8$, which may be the same or different from each other, each represents a hydrogen atom, a halogen atom, an alkyl group, an alkoxy group, an alkylthio group, a ureido group, a carbonamido group, or a sulfonamido group; $R_9$ represents a carbamoyl group, or an alkoxycarbonyl group; $R_{10}$ represents a hydrogen atom, a halogen atom, an alkyl group, an alkoxy group, or an alkylthio group; and * indicates the position at which BALL is bonded;

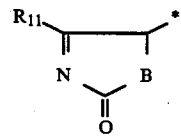
(VII)

wherein $R_{11}$ represents an alkyl group, an aryl group, an anilino group, an alkylamino group, or an alkoxy group; and B represents an oxygen atom, a sulfur atom or a nitrogen atom; and * indicates the position at which BALL is bonded;

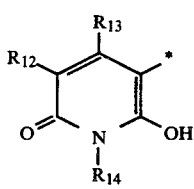

wherein $R_{12}$ and $R_{13}$ each represents a hydrogen atom, a cyano group, an alkoxycarbonyl group, a carbamoyl group, a sulfo group, or an acyl group; $R_{14}$ represents a hydrogen atom, an alkyl group, an aryl group, or a heterocyclic group; and * indicates the position at which BALL is bonded;

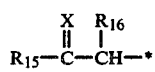

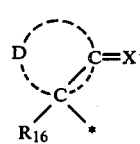

wherein $R_{15}$ represents an alkyl group, an aryl group, a heterocyclic group, a cyano group, a hydroxyl group, an alkoxy group, an aryloxy group, a heterocyclic oxy group, an alkylamino group, a dialkylamino group, an anilino group, a sulfonyl group, a sulfamoyl group or an ammonium group; $R_{16}$ represents a hydrogen atom, an alkyl group, an aryl group, a halogen atom, an alkoxy group, an acyloxy group or a heterocyclic group; X represents an oxygen atom or $=N-R_{17}$, wherein $R_{17}$ represents an alkyl group, an aryl group, a hydroxyl group, an alkoxy group, or a sulfonyl group; D represents a non-metallic atomic group forming a 5- to 7-membered carbocyclic ring (e.g., indanone ring, cyclopentanone ring or cyclohexanone ring) or heterocyclic ring (e.g., piperidone ring, pyrrolidone ring or hydrocarbostyril ring) together with the moiety of

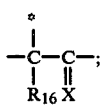

and * indicates the position at which BALL is bonded; and

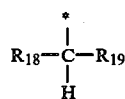

wherein $R_{18}$ and $R_{19}$, which may be the same or different from each other, each represents an alkoxycarbonyl group, a carbamoyl group, an acyl group, a cyano group, a formyl group, a sulfonyl group, a sulfinyl group, a sulfamoyl group, an ammoniumyl group or an

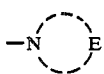

group, wherein E represents a non-metallic atomic group forming a 5- to 7-membered heterocyclic ring, e.g., a phthalimide ring, a triazole ring, or a tetrazole ring, together with

and * indicates the position at which BALL is bonded.

In the above-described formulae (II) to (XI), FOG is bonded to any of the positions of $R_1$ to $R_{19}$, A, B and D. The total molecular weight of COUP and FOG is preferably less than 500, and more preferably less than 400.

Preferred examples of BALL according to the present invention include an alkoxy group, an alkylthio group, an acyloxy group, and groups represented by formulae (XII) to (XVIII):

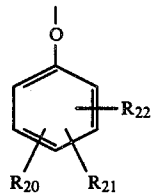

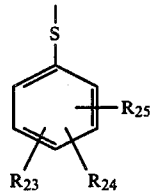

wherein $R_{20}$, $R_{21}$ and $R_{22}$, which may be the same or different from each other, each represents a hydrogen atom, a halogen atom, an alkyl group, an aryl group, an alkoxy group, an alkylthio group, a carbonamido group, a sulfonamido group, an acyl group, a sulfinyl group, a sulfonyl group, an alkoxycarbonyl group, an alkoxysulfonyl group, a carbamoyl group, a sulfamoyl group, a carboxyl group, a sulfo group, a cyano group, or a nitro group; and $R_{23}$, $R_{24}$ and $R_{25}$, which may be the same or different from each other, each represents a hydrogen atom, a halogen atom, an alkyl group, an aryl group, an alkoxy group, an alkylthio group, an acyl group, an acylamino group, an alkoxycarbonyl group, or an aryloxy group;

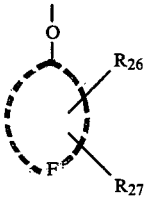

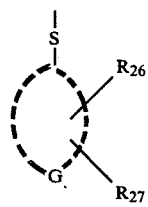
(XV)

wherein F and G each represents a non-metallic atomic group forming a 5- to 7-membered heterocyclic ring (e.g., a triazole ring, a tetrazole ring, a thiadiazole ring or an oxadiazole ring); and $R_{26}$ and $R_{27}$, which may be the same or different from each other, each represents a hydrogen atom, a halogen atom, an alkyl group, an alkoxy group, an aryl group, an alkylthio group, an arylthio group, a carbonamido group, or a sulfonamido group;

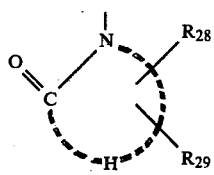
(XVI)

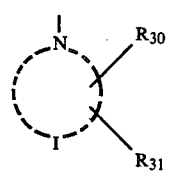
(XVII)

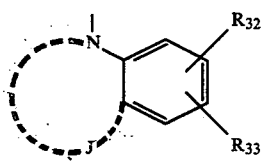
(XVIII)

wherein H represents a non-metallic atomic group forming a 5- to 7-membered heterocyclic ring (e.g., a hydantoin ring, an oxazolidinedione ring or a pyridone ring) together with $$\begin{matrix} O & | \\ \| & \\ -C-N- \end{matrix};$$

I represents a non-metallic atomic group forming an azole ring (e.g., a pyrazole ring, an imidazole ring, a triazole ring or a tetrazole ring) together with

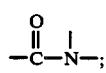;

J represents a non-metallic atomic group necessary for forming an indole ring, an indazole ring, a benzimidazole ring, or a benzotriazole ring together with

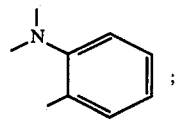;

$R_{28}$ and $R_{29}$, which may be the same or different from each other, each represents a hydrogen atom, a halogen atom, an alkyl group, an aryl group, an alkoxy group, an aryloxy group, an alkylthio group, an arylthio group, an alkylamino group, a dialkylamino group, an anilino group, an alkoxycarbonyl group, a carbamoyl group, a sulfinyl group, a sulfonyl group, an acyloxy group, a carbonamido group, or a sulfonamido group; $R_{30}$ and $R_{31}$, which may be the same or different from each other, each represents a hydrogen atom, a halogen atom, an alkyl group, an alkoxy group, an aryl group, an alkylthio group, an alkoxycarbonyl group, a carbamoyl group, a cyano group, an aryloxy group, a carbonamido group, a sulfonamido group, or a ureido group; and $R_{32}$ and $R_{33}$, which may be the same or different, each represents a hydrogen atom, a halogen atom, an alkyl group, an aryl group, an alkoxy group, an aryloxy group, an alkylthio group, an arylthio group, an alkoxycarbonyl group, an aryloxycarbonyl group, a carbamoyl group, a carbonamido group, a sulfonamido group, a sulfamoyl group, or a ureido group.

In the above-described formulae (XII) to (XVIII), the total number of carbon atoms contained in each substituent is generally from 8 to 32, and preferably from 12 to 24.

Preferred examples of FOG which can preferably be used in the present invention include groups represented by formulae (XIX), (XX) and (XXI)

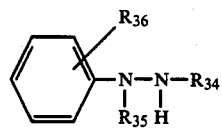
(XIX)

wherein $R_{34}$ represents an acyl group having 1 to 8 carbon atoms (e.g., a formyl group, an acetyl group, a trifluoroacetyl group, a benzoyl group etc.), a sulfonyl group having 1 to 8 carbon atoms (e.g., a methanesulfonyl group, an ethanesulfonyl group, a benzenesulfonyl group, etc.), or an alkoxycarbonyl group having 2 to 8 carbon atoms (e.g., a methoxycarbonyl group); $R_{35}$ represents a hydrogen atom, an alkoxycarbonyl group having 2 to 8 carbon atoms or an acyl group having 1 to 8 carbon atoms; and $R_{36}$ represents a hydrogen atom, an alkyl group having 1 to 8 carbon atoms, an alkoxy group having 1 to 8 carbon atoms, or a halogen atom;

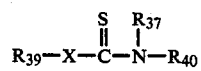
(XX)

wherein X represents an alkylene group having 1 to 4 carbon atoms, an alkenylene group having 2 to 4 carbon atoms, an arylene group having 6 to 10 carbon atoms, —O—, —S—, or

$R_{37}$ and $R_{38}$, which may be the same or different, each represents a hydrogen atom, an alkyl group having 1 to 8 carbon atoms, an aryl group having 6 to 10 carbon atoms or an acyl group having 1 to 8 carbon atoms; and $R_{39}$ and $R_{40}$, which may be the same or different, each represents a hydrogen atom or an alkyl group having 1 to 4 carbon atoms or a chemical bond of X or N;

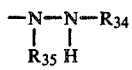 (XXI)

where $R_{34}$ and $R_{35}$ are as defined above in formula (XIX).

The group represented by the formula (XIX) may be bonded to COUP at any position of $R_{34}$, $R_{35}$, $R_{36}$ and the phenyl ring via a divalent linking group (e.g., an alkylene group, an alkenylene group, an arylene group, —O—, —S—, a carbonyl group, a sulfonyl group or an imino group). The moiety

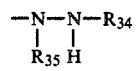

of formula (XXI) can be employed when COUP contains a bondable aryl ring and may be directly bonded to the aryl ring of COUP. The group represented by formula (XX) can be bonded to COUP at the position of $R_{37}$ via a divalent linking group as enumerated with respect to formula (XIX) when $R_{39}$ and $R_{40}$ do not represent a chemical bond of X or N, or the moiety

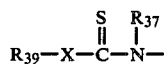

or

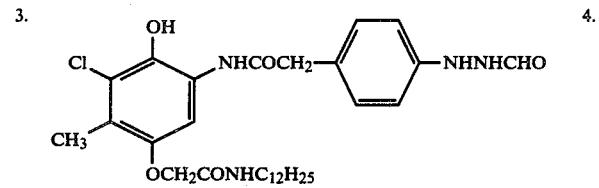

may be directly bonded to COUP.

Specific examples of the compounds according to the present invention are shown below.

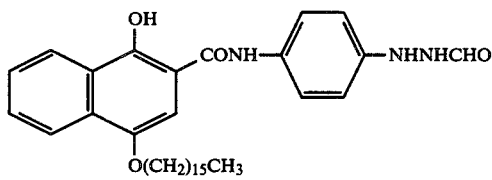

1.

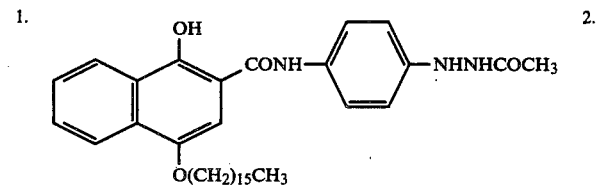

2.

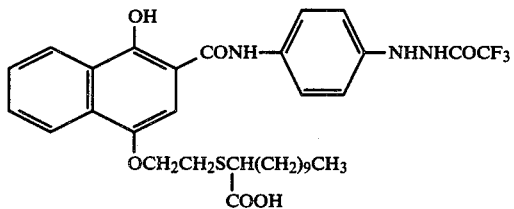

3.

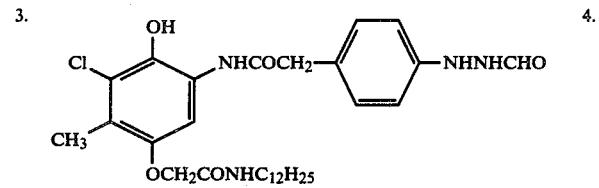

4.

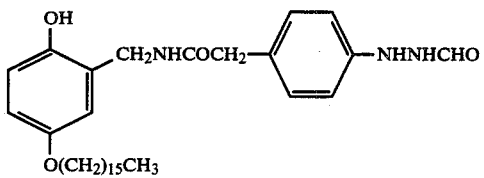

5.

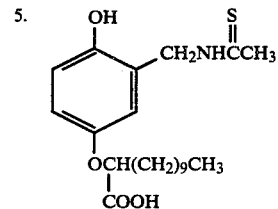

6.

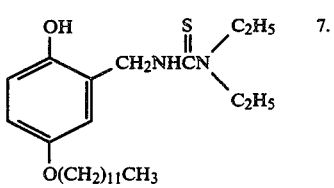

7.

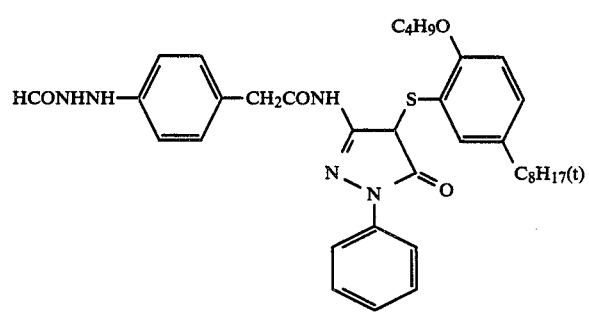

8.

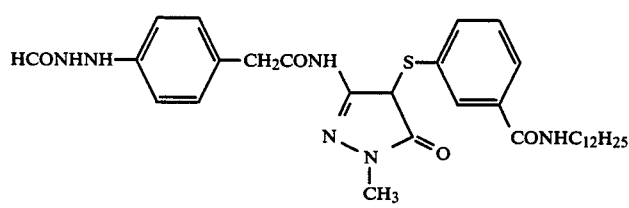
9.
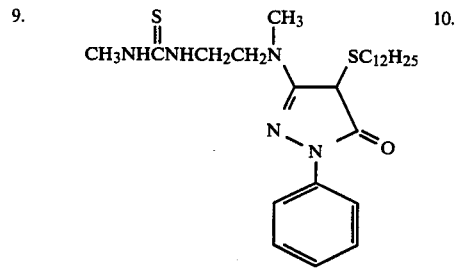
10.
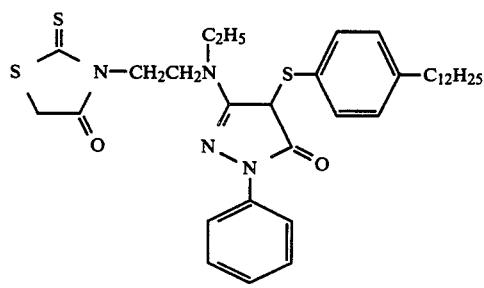
11.
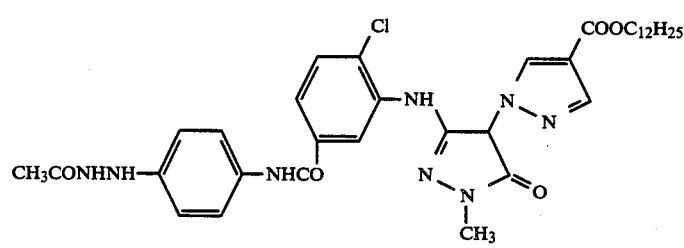
12.
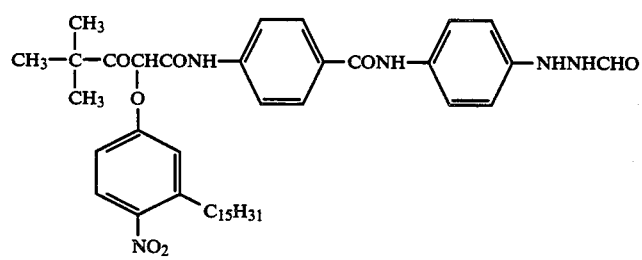
13.
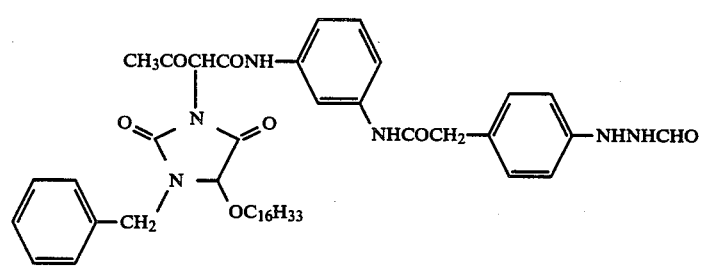
14.
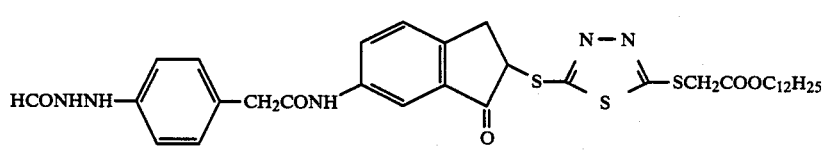
15.

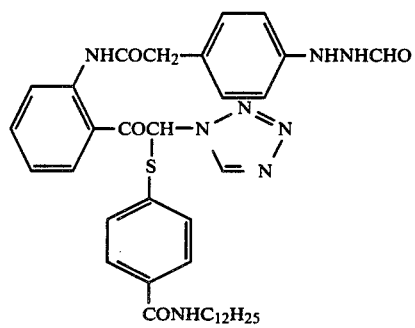

16.

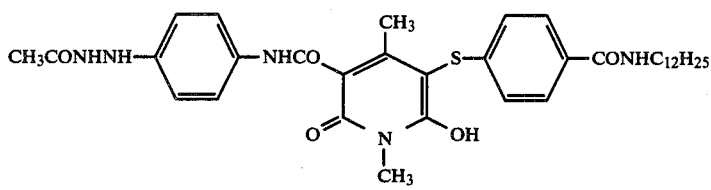

17.

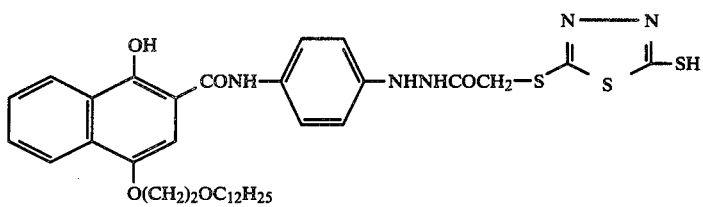

18.

The couplers used in the present invention can be synthesized from known compounds obtained by the method described in U.S. Pat. No. 4,390,618, or U.S. Pat. application Ser. No. 532,631 (filed on Sept. 15, 1983). A typical example of the synthesis is shown by the following reaction scheme:

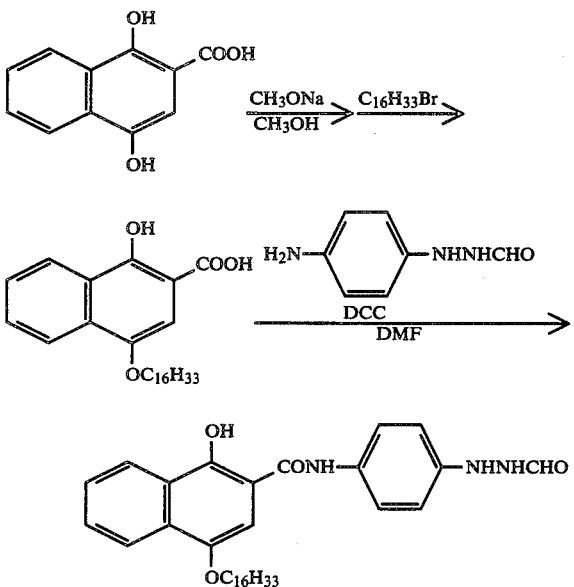

The 1-formyl-2-(4-nitrophenyl)hydrazine used in the above-described reaction scheme can be synthesized according to the method as described in U.S. Pat. No. 4,266,013.

An example of the synthesis of the coupler of this invention is given below.

SYNTHESIS EXAMPLE

Synthesis of Compound (1)

46 g of 4-nitrophenylhydrazine was added to 160 ml of acetonitrile, and 32.2 g of formic acid was slowly added thereto at a temperature of 60° C. The reaction mixture immediately turned homogeneous and then crystals were again precipitated. The reaction was continued for an additional 2 hours at a temperature of 80° C., followed by cooling. The precipitated crystals were filtered, washed with acetonitrile and dried to obtain 49.5 g of 1-formyl-2-(4-nitrophenyl)hydrazine. Melting Point: 184°–186° C.

30 g of the 1-formyl-2-(4-nitrophenyl)hydrazine was then catalytically reduced in 1.6 liters of ethanol in the presence of palladium-on-carbon as a catalyst at room temperature. The reaction mixture was filtered, and the filtrate was evaporated to dryness to obtain 20.5 g of 1-formyl-2-(4-aminophenyl)hydrazine as a white solid. Melting Point: 123°–125° C.

12.3 g of 1,4-dihydroxy-2-naphthoic acid was dissolved in 100 ml of dimethylformamide, and to the solution was added 23.2 g of a 28% methanolic solution of sodium methylate in a nitrogenous atmosphere at 40° C. with stirring. The mixture was heated to 60° C., and 15.3 g of hexadecyl bromide was added thereto dropwise over a period of 30 minutes. The resulting mixture was heated for 3 hours while stirring, cooled, and then poured into 1 liter of ice-water to which 50 ml of concentrated hydrochloric acid had already been added with stirring. The precipitated crude crystals were filtered and washed with water. After addition of 1 g of activated carbon, the mixture was dissolved in 100 ml of methanol while heating. The activated carbon was filtered, and the filtrate was cooled. The precipitated crystals were filtered, washed with methanol and dried to obtain 9.4 g of 1-hydroxy-4-hexadecyloxy-2-naphthoic acid. Melting Point: 121°–124° C.

4.29 g of 1-hydroxy-4-hexadecyloxy-2-naphthoic acid and 1.51 g of 1-formyl-2-(4-aminophenyl)hydrazine were dissolved in 30 ml of dimethylformamide, and to the resulting solution was added dropwise 5 ml of a dimethylformamide solution containing 2.06 g of dicyclohexylcarbodiimide in a nitrogen atmosphere at 0° C. over about 30 minutes. The reaction mixture was stirred at that temperature for 1 hour and then at room temperature for 3 hours. The thus-formed dicyclohexylurea was filtered, and 100 ml of ethyl acetate was added thereto, followed by washing three times with 200 ml portions of water. The ethyl acetate solution was dried over sodium sulfate and then concentrated. The concentrate was dissolved in 100 ml of ethanol under heating, followed by crystallization to obtain 4.40 g of the desired Compound 1. Melting Point: 146°–166° C. Elementary Analysis for $C_{34}H_{47}N_3O_4$

|  | H | C | N |
|---|---|---|---|
| Calculated (%): | 8.43 | 72.70 | 7.48 |
| Found (%): | 8.56 | 72.54 | 7.46 |

The couplers according to the present invention can be used for any typical kind of silver halide color photographic light-sensitive materials including, for example, color negative films, color papers, color positive films, color reversal films for slides, color reversal films for motion picture and color reversal films for television, etc. The couplers are particularly effective for color negative or reversal films which are required to possess both high sensitivities and high image qualities.

Since the coupler center, COUP, can be selected from a wide variety of groups, the couplers according to the present invention can be incorporated into any of a cyan coupler containing layer, a magenta coupler-containing layer, and a yellow coupler containing layer.

With the rise in the price of silver, which is a raw material for photographic light-sensitive materials, a reduction in the amount of silver to be used in the photographic light-sensitive materials has become very important. From this point of view, it has been proposed to make use of dyes in X-ray films, which typically require a large quantity of silver. The couplers according to the present invention are extremely effective materials for the photographic light-sensitive materials, including such X-ray films, because of their contribution to effective use of silver and rapid processing.

The photographic emulsion layers of the photographic light-sensitive materials of the present invention may contain, in addition to the couplers of the present invention, ordinary color-forming couplers, i.e., compounds capable of developing colors upon oxidative coupling with aromatic primary amine developing agents (e.g., phenylenediamine derivatives, aminophenol derivatives, etc.) during the course of color development processing. Examples of such couplers include magenta couplers, such as 5-pyrazolone couplers, pyrazolobenzimidazole couplers, cyanoacetylcoumarone couplers, open chain acylacetonitrile couplers, etc.; yellow couplers, such as acylacetamide couplers (e.g., benzoylacetanilides, pivaloylacetanilides, etc.), etc.; and cyan couplers, such as naphthol couplers, phenol couplers, etc. It is preferable that these couplers contain a hydrophobic group called a ballast group in the molecule, or that these couplers are polymeric non-diffusible couplers. They may be either 2-equivalent or 4-equivalent couplers per silver ion. It is also possible to use couplers capable, upon development, of forming a diffusible dye, such as those described in British Pat. No. 2,083,640A. Other examples of usable couplers include colored couplers capable of exerting color correction effects, couplers capable of releasing development inhibitors during the course of development (so-called DIR couplers), as well as non-color-forming DIR coupling compounds capable of releasing development inhibitors and forming colorless coupling products.

In addition to these couplers, the photographic light-sensitive materials of the present invention may further contain non-color-forming couplers capable of forming colorless coupling products, infrared couplers capable of forming dyes which absorb infrared rays upon the coupling reaction, black color-forming couplers capable of forming black dye images upon the coupling reaction, or the like.

Furthermore, couplers which release coupling components as described in Japanese Patent Application (OPI) Nos. 111536/82 and 111537/82 and couplers which release groups capable of being subjected to an oxidation-reduction reaction with an oxidation product of a color developing agent as described in Japanese Patent Application (OPI) No. 138636/82 may also be used for the purpose of improving photographic properties such as graininess, color reproducibility, etc.

Specific examples of magenta color-forming couplers usable in the present invention include those described in U.S. Pat. Nos. 2,600,788, 2,983,608, 3,062,653, 3,127,267, 3,311,476, 3,419,391, 3,519,429, 3,558,319, 3,582,322, 3,615,506, 3,834,908, 3,891,445, 3,926,631, 3,928,044, 4,076,533, 4,189,321 and 4,220,470, West German Pat. No. 1,810,464, West German Patent Application (OLS) Nos. 2,408,665, 2,417,945, 2,418,959, 2,424,467, 2,536,191, 2,651,363, 2,935,848 and 2,944,601, Japanese Patent Publication Nos. 6031/65, 38498/79, 10901/80, 29420/80 and 29421/81, and Japanese Patent Application (OPI) Nos. 74027/74, 129538/74, 60233/75, 159336/75, 20826/76, 26541/76, 36938/76, 105820/76, 42121/77, 58922/77, 9122/78, 55122/78, 48540/79, 80744/79, 62454/80 and 118034/80, etc.

Specific examples of yellow color-forming couplers which can be used in the present invention include those described in U.S. Pat. Nos. 2,875,057, 3,265,506, 3,408,194, 3,551,155, 3,582,322, 3,725,072, 3,891,445, 3,894,875, 3,973,968, 3,990,896, 4,008,086, 4,012,259, 4,022,620, 4,029,508, 4,046,575, 4,057,432, 4,059,447, 4,095,983, 4,133,958, 4,157,919, 4,182,630, 4,186,019, 4,203,768 and 4,206,278, West German Pat. No. 1,547,868, West German Patent Application (OLS) Nos. 2,213,461, 2,219,917, 2,261,361, 2,263,875, 2,414,006, 2,528,638, 2,935,849 and 2,936,842, British Pat. No. 1,425,020, Japanese Patent Publication Nos. 13576/74, 10783/76, 36856/79 and 13023/80, Japanese Patent Application (OPI) Nos. 26133/72, 66835/73, 6341/75, 34232/75, 87650/75, 130442/75, 75521/76, 102636/76, 145319/76, 21827/76, 82424/77, 115219/77, 48541/79, 121126/79, 2300/80, 36900/80, 38576/80 and 70841/80, and *Research Disclosure*, No. 18053, April, 1979, etc.

Specific examples of cyan color-forming couplers which can be used in the present invention include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,758,308, 3,767,411, 4,004,929, 4,052,212, 4,124,396, 4,146,396 and 4,205,990, West German Patent Application (OLS) Nos. 2,214,489, 2,414,830, 2,454,329, 2,634,694, 2,841,166, 2,934,769, 2,945,813, 2,947,707 and 3,005,355, Japanese Patent Publication Nos. 37822/79 and 37823/79, and Japanese Patent Application (OPI) Nos. 5055/73, 59838/73, 130441/75, 26034/76, 146828/76, 69824/77, 90932/77, 52423/78, 105226/78, 110530/78, 14736/79, 48237/79, 66129/79, 13192/79, 32071/80, 65957/80, 73050/80 and 108662/80, etc.

Specific examples of colored couplers usable in the present invention include those described in U.S. Pat. Nos. 2,521,908, 3,034,892 and 3,476,560, West German Patent Application (OLS) No. 2,418,959, Japanese Patent Publication Nos. 22335/63, 11340/67, 2016/69 and 32461/69, and Japanese Patent Application (OPI) Nos. 26034/76 and 42121/77, etc.

Specific examples of DIR couplers usable in the present invention include those described in U.S. Pat. Nos. 3,227,554, 3,617,291, 3,632,345, 3,701,783, 3,790,384, 3,933,500, 3,938,996, 4,052,213, 4,157,916, 4,171,223, 4,183,752, 4,187,110 and 4,226,934, West German Patent Application (OLS) Nos. 2,414,006, 2,454,301, 2,454,329, 2,540,959, 2,707,489, 2,709,688, 2,730,824, 2,754,281, 2,835,073, 2,853,362, 2,855,697 and 2,902,681, British Pat. No. 953,454, Japanese Patent Publication Nos. 16141/76, 2776/78 and 34933/80, Japanese Patent Application (OPI) Nos. 122335/74, 69624/77, 154631/77, 7232/78, 9116/78, 15136/78, 20324/78, 29717/78, 13533/78, 143223/78, 73033/79, 114241/79, 115229/79, 145135/79, 84935/80, 135835/80 and 151944/82, and *Research Disclosure*, No. 18104, etc.

Other examples of usable development inhibitor releasing couplers include those which release development inhibitors with the action of a timing group, as described in U.S. Pat. No. 4,248,962, British Pat. No. 2,072,363, and Japanese Patent Application (OPI) Nos. 56837/82, 154234/82 and 188035/82, etc., and those which release DIR coupler components as described in Japanese Patent Application (OPI) No. 111536/82, etc.

The emulsion layers of the photographic light-sensitive materials of the present invention can further contain a polymeric coupler in combination with the coupler according to the present invention. Specific examples of usable polymeric couplers include those described in U.S. Pat. Nos. 2,698,797, 2,759,816, 2,852,381, 3,163,652, 3,208,977, 3,311,552, 3,299,013, 3,370,952, 3,424,583, 3,451,820, 3,515,557, 3,767,412, 3,912,513, 3,926,436, 4,080,211, 4,128,427 and 4,215,195, *Research Disclosure*, Nos. 17825, 18815 and 19033, British Pat. No. 2,092,573A, and West German Patent Application (OLS) No. 3,217,200A, etc.

The couplers according to the present invention can be used in an amount of from about $10^{-7}$ to 100 mol%, preferably from $10^{-6}$ to 50 mol%, based on the total amount of couplers used. The total amount of couplers used ranges from about $2\times10^{-3}$ to $5\times10^{-1}$ mol, preferably from $1\times10^{-2}$ to $5\times10^{-1}$ mol, per mol of silver.

The couplers of the present invention can be incorporated into silver halide emulsion layers by known methods, such as the method described in U.S. Pat. No. 2,322,027. For example, the couplers can be dissolved in a solvent and then dispersed in a hydrophilic colloid. Examples of solvents usable for this method include organic solvents having a high boiling point, such as alkyl esters of phthalic acid (e.g., dibutyl phthalate, dioctyl phthalate, etc.), phosphoric acid esters (e.g., diphenyl phosphate, triphenyl phosphate, tricresyl phosphate, dioctyl butyl phosphate, etc.), citric acid esters (e.g., tributyl acetyl citrate, etc.), benzoic acid esters (e.g., octyl benzoate, etc.), alkylamides (e.g., diethyl laurylamide, etc.), fatty acid esters (e.g., dibutoxyethyl succinate, dioctyl azelate, etc.), and trimesic acid esters (e.g., tributyl trimesate, etc.); and organic solvents having a boiling point of from about 30° to 150° C., such as lower alkyl acetates (e.g., ethyl acetate, butyl acetate, etc.), ethyl propionate, secondary butyl alcohol, methyl isobutyl ketone, β-ethoxyethyl acetate, methyl cellosolve acetate, etc. Mixtures of the above-described organic solvents having a high boiling point and organic solvents having a low boiling point can also be used.

The incorporation of the couplers of this invention into silver halide emulsion layers may also be carried out by the dispersing method using polymers as described in Japanese Patent Publication No. 39853/76 and Japanese Patent Application (OPI) No. 59943/76.

Of the couplers according to the present invention, those having an acidic group, such as a carboxyl group or a sulfo group, can be introduced into hydrophilic colloids as an aqueous alkaline solution.

In the silver halide emulsion layers of the photographic light-sensitive materials of the present invention, any of silver bromide, silver iodobromide, silver iodochlorobromide, silver chlorobromide and silver chloride can be used, with silver iodobromide being preferred.

The photographic emulsions used in the light-sensitive materials of the present invention can be spectrally sensitized by methine dyes or the like. Such sensitizing dyes can be used either alone or in combination. Combinations of sensitizing dyes can be used for the purpose of supersensitization. In combination with the sensitizing dye, the photographic emulsions may further contain a dye which per se exerts no sensitizing effect or a compound which exhibits no substantial absorptions in the visible region of the spectrum, to attain supersensitizing effect. Examples of useful sensitizing dyes, dyes and compounds for supersensitization and combinations thereof are described in, for example, *Research Disclosure*, Vol. 176, No. 17643, IV-J, page 23 (December 1978).

The hydrophilic colloid layers in the photographic light-sensitive materials of this invention can contain water-soluble dyes as filter dyes or for the purpose of preventing irradiation or for other purposes. Such dyes include oxonol dyes, hemioxonol dyes, styryl dyes, merocyanine dyes, cyanine dyes and azo dyes. Among them, oxonol dyes, hemioxonol dyes and merocyanine dyes are particularly useful.

The photographic emulsion layers of the photographic light-sensitive materials of this invention can further contain such compounds as polyalkylene oxides or derivatives thereof (e.g., ethers, esters, amines, etc.), thioether compounds, thiomorpholines, quaternary ammonium salt compounds, urethane derivatives, urea derivatives, imidazole derivatives and 3-pyrazolidones, in order to increase sensitivity and contrast, or to accelerate development thereof. Examples of such compounds usable include those described in U.S. Pat. Nos. 2,400,532, 2,423,549, 2,716,062, 3,617,280, 3,772,021 and 3,808,003, British Pat. No. 1,488,991, etc.

The photographic emulsions used in the present invention can additionally contain various compounds for the purpose of stabilizing photographic properties or preventing fogs during production, storage or photographic processing thereof. Examples of such antifoggants or stabilizers include azoles, such as benzothiazoliums, nitroindazoles, triazoles, benzotriazoles and benzimidazoles (in particular, nitro- or halogen-substituted benzimidazoles); heterocyclic mercapto compounds, such as mercaptothiazoles, mercaptobenzothiazoles, mercaptobenzimidazoles, mercaptothiadiazoles, mercaptotetrazoles (in particular, 1-phenyl-5-mercaptotetrazole) and mercaptopyrimidines; heterocyclic mercapto compounds as enumerated above containing water-solubilizing groups, e.g., carboxyl and sulfo groups; thioketo compounds, such as oxazolinethiones; azaindenes, such as tetraazaindenes (in particular, 4-hydroxy-substituted(1,3,3a,7)tetraazaindenes); benzenethiosulfonic acids; benzenesulfinic acids; and the like.

In order to prevent color fogs, hydroquinone derivatives, aminophenol derivatives, gallic acid derivatives, ascorbic acid derivatives, etc., may also be incorporated into the photographic light-sensitive materials of the present invention.

In carrying out the present invention, there can be additionally used known color fading preventing agents including hydroquinone derivatives, gallic acid derivatives, p-alkoxyphenols, p-oxyphenol derivatives, bisphenols, and the like. Further, dye image stabilizers usable in the present invention can be used individually or in combination of two or more of them.

In the photographic light-sensitive materials of the present invention, the hydrophilic colloid layers may contain ultraviolet ray absorbing agents. The ultraviolet ray absorbing agents usable include, for example, benzotriazole compounds substituted with an aryl group, 4-thiazolidone compounds, benzophenone compounds, cinnamic acid ester compounds, butadiene compounds, benzoxazole compounds, and ultraviolet ray absorbing polymers. These ultraviolet ray absorbing agents may be fixed in the above-described hydrophilic colloid layers.

The present invention will now be illustrated in greater detail with reference to the following examples, but the present invention is not to be construed as being limited thereto.

EXAMPLE 1

Each of the couplers according to the present invention [Couplers (1) to (3)] and comparative couplers (Couplers C-1 to C-3) was dissolved in a mixture of tricresyl phosphate and ethyl acetate, and the solution was emulsified into an aqueous gelatin solution using a homogenizer. The resulting emulsion was coated together with a silver halide photographic emulsion onto a cellulose triacetate film support to prepare Samples 1 to 6. The amount of each compound coated is shown in parentheses.

(1) Emulsion Layer
A silver iodobromide negative type emulsion (particle size: 1.5μ; iodide content: 10 mol%; coated silver amount: $2.1 \times 10^{-2}$ mol/m$^2$)
Coupler ($1.4 \times 10^{-3}$ mol/m$^2$)
Tricresyl phosphate (2.0 g/m$^2$)
Gelatin (4.0 g/m$^2$)

(2) Protective Layer
Sodium 2,4-dichloro-6-hydroxy-s-triazine (0.05 g/m$^2$)
Gelatin (2.0 g/m$^2$)

These films were subjected to sensitometric exposure with white light and then to the following development processing at a temperature of 38° C. (Condition A).

Alternatively, these films were preserved under the conditions of 40° C. and 75% RH for 7 days followed by the same procedures as Condition A (Condition B).

| 1. Color Development | 2 min 15 sec |
| 2. Bleaching | 6 min 30 sec |
| 3. Washing | 3 min 15 sec |
| 4. Fixing | 6 min 30 sec |
| 5. Washing | 3 min 15 sec |
| 6. Stabilizing | 3 min 15 sec |

The processing solutions used in the above steps had the following compositions:

| Color Developing Solution | |
| --- | --- |
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N—Ethyl-N—β-hydroxyethylamino)-2-methylaniline Sulfate | 4.5 g |
| Water to make | 1 liter |
| Bleaching Solution | |
| Ammonium Bromide | 160.0 g |
| Aqueous Ammonia (28%) | 25.0 ml |
| Sodium Iron Ethylenediaminetetraacetate | 130.0 g |
| Glacial Acetic Acid | 14.0 ml |
| Water to make | 1 liter |
| Fixing Solution | |
| Sodium Tetrapolyphosphate | 2.0 g |
| Sodium Sulfite | 4.0 g |
| Ammonium Thiosulfate (70%) | 175.0 ml |
| Sodium Bisulfite | 4.6 g |
| Water to make | 1 liter |
| Stabilizing Solution | |
| Formalin | 8.0 ml |
| Water to make | 1 liter |

Photographic properties of the samples are shown in Table 1 below.

TABLE 1

| | | Condition A | | Condition B | |
| --- | --- | --- | --- | --- | --- |
| Sample | Coupler | Fog | Relative Sensitivity* | Fog | Relative Sensitivity* |
| 1 (Invention) | (1) | 0.15 | 100 | 0.16 | 98 |
| 2 (Invention) | (2) | 0.15 | 110 | 0.16 | 107 |
| 3 (Invention) | (3) | 0.16 | 120 | 0.17 | 118 |
| 4 (Comparison) | C-1 | 0.12 | 67 | 0.16 | 50 |
| 5 (Comparison) | C-2 | 0.14 | 91 | 0.20 | 83 |
| 6 (Comparison) | C-3 | 0.15 | 100 | 0.22 | 88 |

Note:
*Relative sensitivity: reciprocal of the exposure amount required for obtaining a color density of fog value + 0.2, and the sensitivity of Sample 1 under Condition A is taken as 100 with the other sensitivities being relatively shown.

The comparative couplers used in Example 1 are as follows:

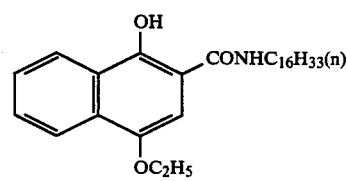

C-1

-continued

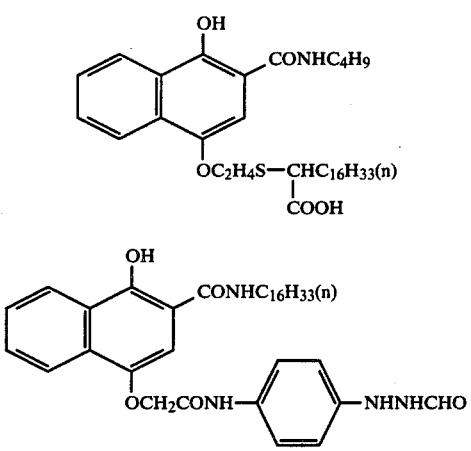

From the results shown in Table 1, it can be seen that the couplers according to the present invention have higher sensitivities than the Comparative Couplers C-1 and C-2, and undergo less decrease in sensitivity and less increase in fog in the forced deterioration testing (Condition B) as compared with any of the Comparative Couplers C-1, C-2 and C-3. Further, microscopic observation revealed that the Processes Samples 1 to 3 have excellent graininess as compared with Comparative Sample 6.

EXAMPLE 2

On a cellulose triacetate film support were coated layers having the compositions set forth below to prepare a multilayer color photographic light-sensitive material.
First Layer: Antihalation Layer
  A gelatin layer containing black colloidal silver
Second Layer: Intermediate Layer
  A gelatin layer containing an emulsified dispersion of 2,5-di-t-octylhydroquinone
Third Layer: First Red-Sensitive Emulsion Layer
  A silver iodobromide emulsion (iodide content: 5 mol%; coated silver amount: 1.6 g/m$^2$)
  Sensitizing Dye I ($6 \times 10^{-4}$ mol per mol of silver)
  Sensitizing Dye II ($1.5 \times 10^{-4}$ mol per mol of silver)
  Coupler EX-1 (0.04 mol per mol of silver)
  Coupler EX-3 (0.003 mol per mol of silver)
  Coupler EX-4 (0.0006 mol per mol of silver)
Fourth Layer: Second Red-Sensitive Emulsion Layer
  A silver iodobromide emulsion (iodide content: 9 mol%; coated silver amount: 1.8 g/m$^2$)
  Sensitizing Dye I ($3 \times 10^{-4}$ mol per mol of silver)
  Sensitizing Dye II ($1.2 \times 10^{-4}$ mol per mol of silver)
  Coupler EX-2 (0.02 mol per mol of silver)
  Coupler EX-4 (0.0016 mol per mol of silver)
Fifth Layer: Intermediate Layer
  The same as Second Layer.
Sixth Layer: First Green-Sensitive Emulsion Layer
  A silver iodobromide emulsion (iodide content: 4 mol%; coated silver amount: 1.2 g/m$^2$)
  Sensitizing Dye III ($3 \times 10^{-4}$ mol per mol of silver)
  Sensitizing Dye IV ($1 \times 10^{-4}$ mol per mol of silver)
  Coupler EX-5 (0.05 mol per mol of silver)
  Coupler EX-6 (0.008 mol per mol of silver)
  Coupler EX-4 (0.0015 mol per mol of silver)
Seventh Layer: Second Green-Sensitive Emulsion Layer
  A silver iodobromide emulsion (iodide content: 8 mol%; coated silver amount: 1.3 g/m$^2$)
  Sensitizing Dye III ($2.5 \times 10^{-4}$ mol per mol of silver)
  Sensitizing Dye IV ($0.8 \times 10^{-4}$ mol per mol of silver)
  Coupler EX-7 (0.017 mol per mol of silver)
  Coupler EX-6 (0.003 mol per mol of silver)
Eighth Layer: Yellow Filter Layer
  A gelatin layer containing yellow colloidal silver and an emulsified dispersion of 2,5-di-t-octylhydroquinone.
Ninth Layer: First Blue-Sensitive Emulsion Layer
  A silver iodobromide emulsion (iodide content: 6 mol%; coated silver amount: 0.7 g/m$^2$)
  Coupler EX-8 (0.25 mol per mol of silver)
  Coupler EX-4 (0.015 mol per mol of silver)
Tenth Layer: Second Blue-Sensitive Emulsion Layer
  A silver iodobromide emulsion (iodide content: 6 mol%; coated silver amount: 0.6 g/m$^2$)
  Coupler Ex-8 (0.06 mol per mol of silver)
Eleventh Layer: First Protective Layer
  A gelatin layer containing silver iodobromide (iodide content: 1 mol%; average particle size: 0.07$\mu$; coated silver amount: 0.3 g/m$^2$) and a dispersion of Ultraviolet Ray Absorbing Agents EX-9 and EX-10.
Twelfth Layer: Second Protective Layer
  A gelatin layer containing polymethyl methacrylate particles (diameter: about 1.5$\mu$).
Gelatin Hardener H-1 and a surface active agent were incorporated into each of the above layers in addition to the above-described components.

The sample thus prepared was designated Sample 201.

SAMPLES 202 AND 203

Samples 202 and 203 were prepared in the same manner as described in Sample 201 except that Coupler EX-2 in the fourth layer of Sample 201 was replaced by an equimole of Coupler (1) or (3) of the present invention.

SAMPLES 204 AND 205

Samples 204 and 205 were prepared in the same manner as described in Sample 201 except that Coupler (6) or Coupler (8) according to the present invention was further added in an amount of $2 \times 10^{-4}$ mol or $1 \times 10^{-5}$ mol per mol of silver, respectively.

A series of Samples 201 to 205 was preserved at room temperature for 14 days (Condition C) and another series of samples was preserved under the conditions of 40° C. and 80% RH for 14 days (Condition D). These samples were exposed to light and then development-processes in the same manner as described in Example 1 except that the color development time was 3 minutes and 15 seconds. The photographic properties of the samples obtained are shown in Table 2.

Further, graininess of each sample under Condition C was measured by a commonly employed RMS method, with an aperture for the measurement of 48 microns. The results obtained are also shown in Table 2.

TABLE 2

| Sample | Coupler | Condition C Minimum Density | Condition C Relative Sensitivity | Condition D Minimum Density | Condition D Relative Sensitivity | Graininess* |
|---|---|---|---|---|---|---|
| 201 (Comparison) | EX-2 | 0.17 | 100 | 0.19 | 86 | 0.035 |
| 202 (Invention) | (1) | 0.17 | 129 | 0.17 | 129 | 0.031 |
| 203 (Invention) | (3) | 0.18 | 152 | 0.18 | 152 | 0.036 |
| 204 (Invention) | EX-2, (6) | 0.19 | 135 | 0.19 | 129 | 0.040 |
| 205 (Invention) | EX-2, (8) | 0.19 | 141 | 0.20 | 135 | 0.042 |

Note:
*RMS value at a density of 0.7.

It can be seen from Table 2 that Samples 202 to 205 containing the couplers according to the present invention exhibit high sensitivities and are stable in the forced deterioration testing (Condition D) as particularly shown by Samples 202 and 203, as compared with Comparative Sample 201. Further, it can be seen that Sample 202 using the coupler of the present invention has excellent graininess as well as high sensitivity, and Sample 203 having a markedly high sensitivity shows graininess substantially equal to that of Comparative Sample 201.

The compounds used for preparing the samples were as follows:

Sensitizing Dye I: Pyridinium salt of anhydro-5,5'-dichloro-3,3'-di($\gamma$-sulfopropyl)-9-ethylthiacarbocyanine hydroxide Sensitizing Dye II: Triethylamine salt of anhydro-9-ethyl-3,3'-di($\gamma$-sulfopropyl)-4,5,4',5'-dibenzothiacarbocyanine hydroxide Sensitizing Dye III: Sodium salt of anhydro-9-ethyl-5,5'-dichloro-3,3'-di($\gamma$-sulfopropyl)oxacarbocyanine Sensitizing Dye IV: Sodium salt of anhydro-5,6,5',6'-tetrachloro-1,1'-diethyl-3,3'-di-{$\beta$-[$\beta$-($\gamma$-sulfopropyl)ethoxy]ethyl}imidazolocarbocyanine hydroxide

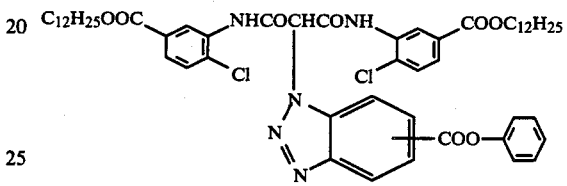

EX-1

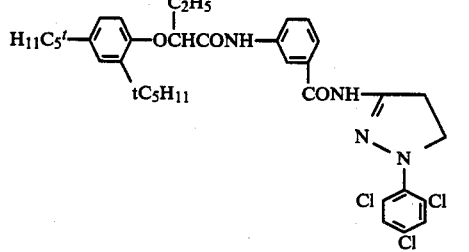

EX-2

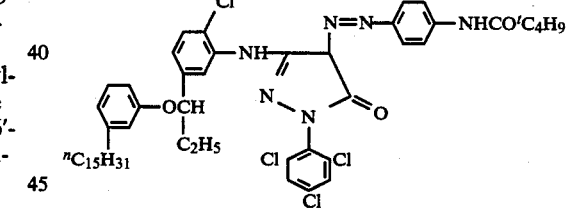

EX-3

-continued

EX-4

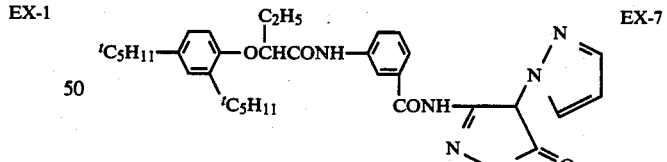

EX-5

EX-6

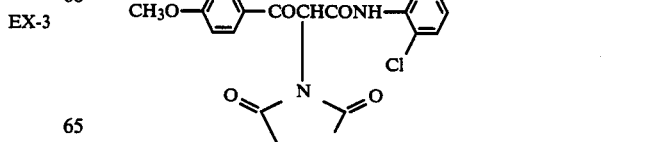

EX-7

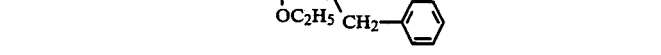

EX-8

A polymer having the following repeating unit:

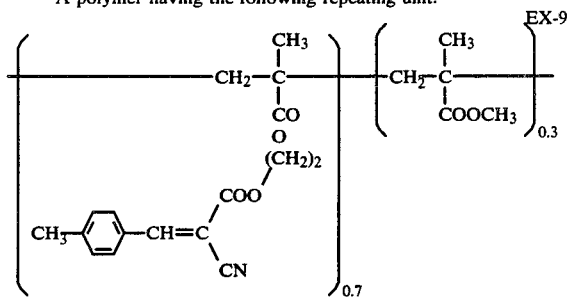
EX-9

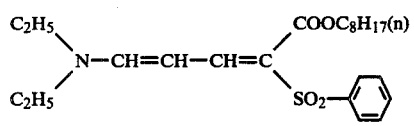
EX-10

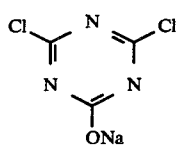
H-1

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon at least one silver halide emulsion layer, wherein at least one silver halide emulsion layer contains a coupler which, when subjected to a coupling reaction with an oxidation product of a color developing agent, produces a diffusible coupling product which exerts a fogging effect in a developing solution, said coupler being represented by formula (I)

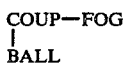  (I)

wherein COUP represents a coupler residue capable of being subjected to a coupling reaction with an oxidation product of an aromatic primary amine developing agent; BALL represents a ballast bonded to the coupling position of COUP and releasable from COUP upon reaction between COUP and an oxidation product of an aromatic primary amine developing agent; and FOG represents a group which manifests a fogging effect in a developing solution after BALL is released upon the reaction between COUP and an oxidation product of an aromatic primary amine developing agent.

2. A silver halide color photographic light-sensitive material as in claim 1, wherein the coupler residue is a residue of a cyan color-forming coupler selected from the group consisting of phenol couplers and naphthol couplers.

3. A silver halide color photographic light-sensitive material as in claim 1, wherein the coupler residue is a residue of a magenta color-forming coupler selected from the group consisting of 5-pyrazolone couplers, pyrazolobenzimidazole couplers, pyrazolotriazole couplers, cyanoacetylcoumarone couplers, and open chain acylacetonitrile couplers.

4. A silver halide color photographic light-sensitive material as in claim 1, wherein the coupler residue is a residue of a yellow color-forming coupler selected from the group consisting of benzoylacetanilide couplers, pivaloylacetanilide couplers, and malondianilide couplers.

5. A silver halide color photographic light-sensitive material as in claim 1, wherein the coupler residue is a residue of a non-color-forming coupler selected from the group consisting of indanones, cyclopentanones, cyclohexanones, malonic acid diesters, acetophenones, imidazolinones, oxazolinones, and thiazolinones.

6. A silver halide color photographic light-sensitive material as in claim 1, wherein the coupler residue is a residue represented by one of formulae (II), (III), (IV), (V), (VI), (VII), (VIII), (IX), (X), and (XI)

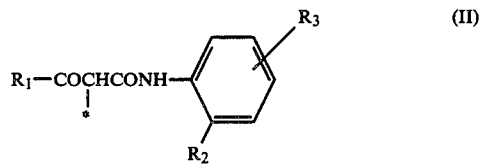  (II)

wherein $R_1$ represents an alkyl group, an aryl group, a heterocyclic group, an alkoxy group, an alkylamino group, or an anilino group; $R_2$ represents a hydrogen atom, a halogen atom, an alkyl group, an alkoxy group, or an aryloxy group; $R_3$ represents a hydrogen atom, an alkyl group, an alkoxy group, an acyl group, an aryloxy group, a sulfonyl group, a carbonamido group, a hydroxyl group, a carboxyl group, a sulfo group, a sulfonamido group, an alkoxycarbonyl group, a carbamoyl group, a sulfamoyl group, a ureido group, or a halogen atom; and * indicates the position at which BALL is bonded;

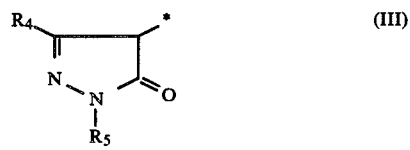  (III)

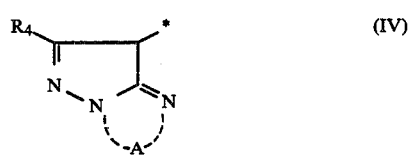  (IV)

wherein $R_4$ represents an alkoxy group, an alkylamino group, a dialkylamino group, an alkyl group, a carbonamido group, or a sulfonamido group; $R_5$ represents an alkyl group, or an aryl group; and A represents a nonmetallic atomic group forming a 5-membered azole ring, and formula (IV) includes tautomers thereof; and * indicates the position at which BALL is bonded;

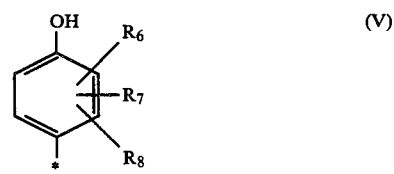  (V)

-continued

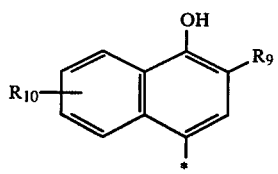 (VI)

wherein $R_6$, $R_7$, and $R_8$, which may be the same or different from each other, each represents a hydrogen atom, a halogen atom, an alkyl group, an alkoxy group, an alkylthio group, a ureido group, a carbonamido group, or a sulfonamido group; $R_9$ represents a carbamoyl group or an alkoxycarbonyl group; $R_{10}$ represents a hydrogen atom, a halogen atom, an alkyl group, an alkoxy group, or an alkylthio group; and * indicates the position at which BALL is bonded;

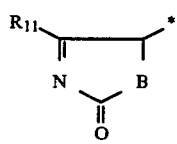 (VII)

wherein $R_{11}$ represents an alkyl group, an aryl group, an anilino group, an alkylamino group, or an alkoxy group; B represents an oxygen atom, a sulfur atom or a nitrogen atom; and * indicates the position at which BALL is bonded;

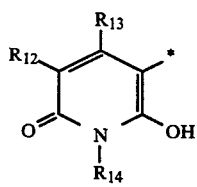 (VIII)

wherein $R_{12}$ and $R_{13}$ each represents a hydrogen atom, a cyano group, an alkoxycarbonyl group, a carbamoyl group, a sulfo group, or an acyl group; $R_{14}$ represents a hydrogen atom, an alkyl group, an aryl group or a heterocyclic group; and * indicates the position at which BALL is bonded;

 (IX)

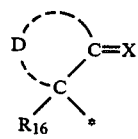 (X)

wherein $R_{15}$ represents an alkyl group, an aryl group, a heterocyclic group, a cyano group, a hydroxyl group, an alkoxy group, an aryloxy group, a heterocyclic oxy group, an alkylamino group, a dialkylamino group, an anilino group, a sulfonyl group, a sulfamoyl group, or an ammonium group; $R_{16}$ represents a hydrogen atom, an alkyl group, an aryl group, a halogen atom, an alkoxy group, an acyloxy group, or a heterocyclic group; X represents an oxygen atom or $=N-R_{17}$, wherein $R_{17}$ represents an alkyl group, an aryl group, a hydroxyl group, an alkoxy group, or a sulfonyl group; D represents a non-metallic atomic group forming a 5- to 7-membered carbocyclic ring or heterocyclic ring together with the moiety of

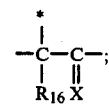

and * indicates the position at which BALL is bonded; and

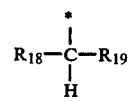 (XI)

wherein $R_{18}$ and $R_{19}$, which may be the same or different from each other, each represents an alkoxycarbonyl group, a carbamoyl group, an acyl group, a cyano group, a formyl group, a sulfonyl group, a sulfinyl group, a sulfamoyl group, an ammonium group or an

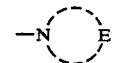

group, wherein E represents a non-metallic atomic group forming a 5- or 7-membered heterocyclic ring together with —N; and * indicates the position at which BALL is bonded, and wherein in formulas (II) to (XI), FOG is bonded to any of the positions $R_1$ to $R_{19}$, A, B and D.

7. A silver halide color photographic light-sensitive material as in claim 1, wherein the group represented by BALL is an alkoxy group, an alkylthio group, an acyloxy group, or a group represented by one of formulae (XII), (XIII), (XIV), (XV), (XVI), (XVII), and (XVIII)

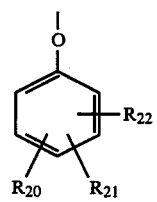 (XII)

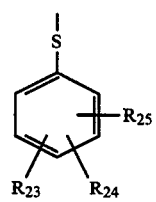 (XIII)

wherein $R_{20}$, $R_{21}$ and $R_{22}$, which may be the same or different from each other, each represents a hydrogen atom, a halogen atom, an alkyl group, an aryl group, an alkoxy group, an alkylthio group, a carbonamido group, a sulfonamido group, an acyl group, a sulfinyl group, a sulfonyl group, an alkoxycarbonyl group, an alkoxysulfonyl group, a carbamoyl group, a sulfamoyl group, a carboxyl group, a sulfo group, a cyano group, or a nitro group; and $R_{23}$, $R_{24}$, and $R_{25}$, which may be the same or different from each other, each represents a hydrogen atom, a halogen atom, an alkyl group, an aryl group, an alkoxy group, an alkylthio group, an acyl group, an acylamino group, an alkoxycarbonyl group, or an aryloxy group;

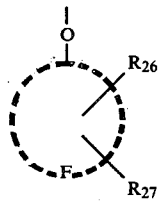
(XIV)

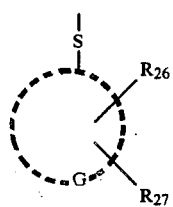
(XV)

wherein F and G each represents a non-metallic atomic group forming a 5- to 7-membered heterocyclic ring; and $R_{26}$ and $R_{27}$, which may be the same or different from each other, each represents a hydrogen atom, a halogen atom, an alkyl group, an alkoxy group, an aryl group, an alkylthio group, an arylthio group, a carbonamido group, or a sulfonamido group;

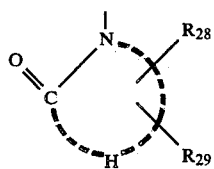
(XVI)

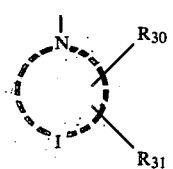
(XVII)

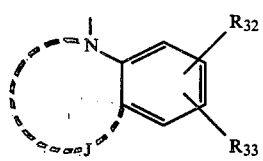
(XVIII)

wherein H represents a non-metallic atomic group forming a 5- to 7-membered heterocyclic ring together with

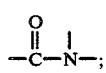

I represents a non-metallic atomic group forming an azole ring together with

J represents a non-metallic atomic group forming an indole ring, an indazole ring, a benzimidazole ring, or a benzotriazole ring together with

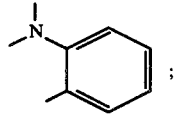

$R_{28}$ and $R_{29}$, which may be the same or different from each other, each represents a hydrogen atom, a halogen atom, an alkyl group, an aryl group, an alkoxy group, an aryloxy group, an alkylthio group, an arylthio group, an alkylamino group, a dialkylamino group, an anilino group, an alkoxycarbonyl group, a carbamoyl group, a sulfinyl group, a sulfonyl group, an acyloxy group, a carbonamido group, or a sulfonamido group; $R_{30}$ and $R_{31}$, which may be the same or different from each other, each represents a hydrogen atom, a halogen atom, an alkyl group, an alkoxy group, an aryl group, an alkylthio group, an alkoxycarbonyl group, a carbamoyl group, a cyano group, an aryloxy group, a carbonamido group, a sulfonamido group, or a ureido group; and $R_{32}$ and $R_{33}$, which may be the same or different, each represents a hydrogen atom, a halogen atom, an alkyl group, an aryl group, an alkoxy group, an aryloxy group, an alkylthio group, an arylthio group, an alkoxycarbonyl group, an aryloxycarbonyl group, a carbamoyl group, a carbonamido group, a sulfonamido group, a sulfamoyl group, or a ureido group.

8. A silver halide color photographic light-sensitive material as in claim 1, wherein the coupler is present in an amount of from about $10^{-7}$ to 100 mol% based on the total amount of couplers present in the material.

9. A silver halide color photographic light-sensitive material as in claim 8, wherein the coupler is present in an amount of from $10^{-6}$ to 50 mol% based on the total amount of couplers present in the material.

10. A silver halide color photographic light-sensitive material as in claim 1, wherein the coupler is present in an amount of from about $10^{-7}$ to 100 mol% based on the total amount of couplers present in the material.

11. A silver halide color photographic light-sensitive material as in claim 1, wherein the coupler is present in an amount of from $10^{-6}$ to 50 mol% based on the total amount of couplers present in the material.

12. A silver halide color photographic light-sensitive material as in claim 6, wherein the coupler is present in an amount of from about $10^{-7}$ to 100 mol% based on the total amount of couplers present in the material.

13. A silver halide color photographic light-sensitive material as in claim 6, wherein the coupler is present in an amount of from $10^{-6}$ to 50 mol% based on the total amount of couplers present in the material.

14. A silver halide color photographic light-sensitive material as in claim 7, wherein the coupler is present in an amount of from about $10^{-7}$ to 100 mol% based on the total amount of couplers present in the material.

15. A silver halide color photographic light-sensitive material as in claim 7, wherein the coupler is present in an amount of from $10^{-6}$ to 50 mol% based on the total amount of coupler present in the material.

16. A silver halide color photographic light sensitive material as in claim 1, wherein the group represented by FOG is a group represented by one of formulae (XIX), (XX), and (XXI)

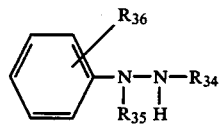 (XIX)

wherein $R_{34}$ represents an acyl group, a sulfonyl group, or an alkoxycarbonyl group; $R_{35}$ represents a hydrogen atom, an alkoxycarbonyl group, or an acyl group; and $R_{36}$ represents a hydrogen atom, an alkyl group, an alkoxy group, or a halogen atom;

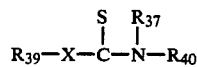 (XX)

wherein X represents an alkylene group having 1 to 4 carbon atoms, an alkenylene group having 2 to 4 carbon atoms, an arylene group having 6 to 10 carbon atoms, —O—, —S—, or

$R_{37}$ and $R_{38}$, which may be the same or different, each represents a hydrogen atom, an alkyl group having 1 to 8 carbon atoms, an aryl group having 6 to 10 carbon atoms or an acyl group having 1 to 8 carbon atoms; and $R_{39}$ and $R_{40}$, which may be the same or different, each represents a hydrogen atom or an alkyl group having 1 to 4 carbon atoms or a chemical bond of X or N;

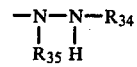 (XXI)

where $R_{34}$ and $R_{35}$ are as defined in formula (XIX); and wherein the group represented by the formula (XIX) may be bonded to COUP at any position of $R_{34}$, $R_{35}$, $R_{36}$ and the phenyl ring via a divalent linking group selected from an alkylene group, an alkenylene group, an arylene group, —O—, —S—, a carbonyl group, a sulfonyl group, or an imino group; wherein the group represented by formula (XX) can be bonded to COUP at the position of $R_{37}$ via a divalent linking group selected from an alkylene group, an alkenylene group, an arylene group, —O—, —S—, a carbonyl group, a sulfonyl group or an imino group where $R_{39}$ and $R_{40}$ do not represent said chemical bond of X or N, or the moiety

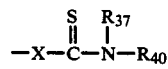

may be directly bonded to COUP when $R_{39}$ represents a chemical bond of X, or the moiety

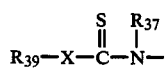

may be directly bonded to COUP when $R_{40}$ represents a chemical bond of N; and wherein when FOG is represented by formula (XXI) COUP contains a bondable aryl ring and the moiety of formula (XXI) is directly bondable to the aryl ring of COUP.

17. A silver halide color photographic light-sensitive material as in claim 16, wherein the coupler is present in an amount of from about $10^{-7}$ to 100 mol% based on the total amount of couplers present in the material.

18. A silver halide color photographic light-sensitive material as in claim 16, wherein the coupler is present in an amount of from $10^{-6}$ to 50 mol% based on the total amount of couplers present in the material.

* * * * *